United States Patent
Shirahata et al.

(10) Patent No.: US 10,014,160 B2
(45) Date of Patent: Jul. 3, 2018

(54) SCANNING ELECTRON MICROSCOPE AND METHOD FOR CONTROLLING SAME

(71) Applicant: Hitachi High-Technologies Corporation, Tokyo (JP)

(72) Inventors: Kaori Shirahata, Tokyo (JP); Daisuke Bizen, Tokyo (JP); Makoto Sakakibara, Tokyo (JP); Yasunari Sohda, Tokyo (JP); Hajime Kawano, Tokyo (JP); Hideyuki Kazumi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/304,869

(22) PCT Filed: Apr. 20, 2015

(86) PCT No.: PCT/JP2015/061936
§ 371 (c)(1),
(2) Date: Oct. 18, 2016

(87) PCT Pub. No.: WO2015/163266
PCT Pub. Date: Oct. 29, 2015

(65) Prior Publication Data
US 2017/0186583 A1    Jun. 29, 2017

(30) Foreign Application Priority Data
Apr. 21, 2014    (JP) .................... 2014-087432

(51) Int. Cl.
*H01J 37/28*    (2006.01)
*H01J 37/26*    (2006.01)
*G01N 23/2251*  (2018.01)

(52) U.S. Cl.
CPC .......... *H01J 37/28* (2013.01); *G01N 23/2251* (2013.01); *H01J 37/263* (2013.01);
(Continued)

(58) Field of Classification Search
CPC .......... H01J 37/10; H01J 37/12; H01J 37/263; H01J 37/28; H01J 2237/2602;
(Continued)

(56) References Cited

U.S. PATENT DOCUMENTS

| 3,952,227 A * | 4/1976 | Van Alphen | .......... H01J 29/465 |
|---|---|---|---|
| | | | 313/432 |
| 2003/0127604 A1* | 7/2003 | Todokoro | .............. H01J 37/244 |
| | | | 250/436 |

(Continued)

FOREIGN PATENT DOCUMENTS

| JP | 2000-299080 A | 10/2000 |
|---|---|---|
| JP | 2001-236916 A | 8/2001 |

(Continued)

OTHER PUBLICATIONS

L. Reimer, "Scanning Electron Microscopy", Springer (1998).
International Search Report of PCT/JP2015/061936 dated Jun. 30, 2015.

*Primary Examiner* — Eliza Osenbaugh-Stewart
(74) *Attorney, Agent, or Firm* — Mattingly & Malur, PC

(57) ABSTRACT

The scanning electron microscope includes: an electron source; a first deflector for deflecting a primary electron beam emitted from the electron source; a second deflector for focusing the primary electron beam deflected by the first deflector and deflecting a second electron from a sample, which is generated the focused primary electron beam, to the outside of the optical axis; a voltage applying unit for applying a negative voltage to the sample to decelerate the primary electron beam; a spectrometer for dispersing the secondary electron; a detector for detecting the secondary electron passing through the spectrometer; an electrostatic lens provided between the second deflector and the spectrometer; and a voltage control unit that controls the voltage (Continued)

applied to the electrostatic lens based on the negative voltage applied to the sample. The electrostatic lens allows the deflecting action to be overlapped with the converging action.

20 Claims, 7 Drawing Sheets

(52) U.S. Cl.
CPC ... *H01J 2237/2602* (2013.01); *H01J 2237/28* (2013.01); *H01J 2237/2801* (2013.01); *H01J 2237/2806* (2013.01)

(58) Field of Classification Search
CPC .......... H01J 2237/28; H01J 2237/2801; H01J 2237/2806; G01N 23/2251
See application file for complete search history.

(56) References Cited

U.S. PATENT DOCUMENTS

| | | | |
|---|---|---|---|
| 2010/0163725 A1* | 7/2010 | Barkshire | H01J 37/05 250/305 |
| 2010/0320382 A1 | 12/2010 | Almogy et al. | |
| 2011/0163229 A1* | 7/2011 | Frosien | H01J 37/05 250/310 |

FOREIGN PATENT DOCUMENTS

| | | |
|---|---|---|
| JP | 2002-139464 A | 5/2002 |
| JP | 2010-519698 A | 6/2010 |

\* cited by examiner

SCANNING ELECTRON MICROSCOPE AND METHOD FOR CONTROLLING SAME

TECHNICAL FIELD

The present invention relates to a scanning electron microscope that produces an image by the signal of electrons such as secondary electrons from a sample by irradiating the sample with an electron beam while scanning the electron beam. More particularly, the present invention relates to a spectroscopic technique for detecting secondary electrons by discriminating them by energy.

BACKGROUND ART

Currently, the scanning electron microscope (hereinafter, SEM) is widely used in observation of submicron- and nano-sized samples. The SEM is designed to form an image by irradiating a sample with primary electrons emitted from an electron source while scanning the primary electrons, and by detecting secondary electrons that are generated in the sample. Here, the secondary electrons can be grouped into "true" secondary electrons characterized by having an energy of 50 eV or less, and backscattered electrons having an energy nearly equal to the incident energy of the primary electron. It is possible to obtain the contrast that reflects the differences in the shape of the pattern surface, the potential, the work function, and the like from the "true" secondary electron. On the other hand, it is possible to obtain the contrast that reflects the difference in the pattern material from the backscattered electron (See Non-patent Literature 1).

Recently, SEMs developed by different companies have included a plurality of detectors, enabling users to obtain images with various contrasts. On the other hand, it is difficult to interpret the image contrast and there is an increased demand for a quantitative analysis of the energy of secondary electrons detected by the SEM. In addition, it is necessary to perform an energy analysis on the secondary electrons under the condition in which the energy of the primary electrons is low, in order to reduce the damage to the sample caused by primary electron irradiation. As a method for performing the energy dispersion of secondary electrons in SEM, for example there is known a method described in Patent Literature 1.

CITATION LIST

Patent Literature

Patent Literature 1: Japanese Unexamined Patent Application Publication No. 2001-236916

Non-Patent Literature

Non-patent Literature 1: L. Reimer: "Scanning Electron Microscopy" Springer (1998)

SUMMARY OF INVENTION

Technical Problem

In the method disclosed in Patent Literature 1, the energy dispersion of the secondary electron is performed by placing a spectrometer between an objective lens of an SEM and a sample. However, in such a configuration, it is difficult to reduce the distance between the objective lens and the sample. As a result, there is a problem that the spatial resolution of a primary electron is deteriorated.

The retarding method that applies a negative voltage $V_r$ (<0) to a sample to decelerate the primary electron immediately above the sample is an effective method for obtaining a high spatial resolution under the condition in which the energy of the primary electron is low. In the retarding method, a voltage $V_r$ of several kV is typically applied to the sample. In this case, the secondary electrons generated in the sample are accelerated by the retarding voltage $V_r$, and most of the secondary electrons pass through the objective lens which is the converging lens. In other words, when the retarding method is applied to the configuration disclosed in Patent Literature 1, there would be very few secondary electrons injected into the spectrometer.

Thus, in order to perform an energy analysis of secondary electrons in the SEM to which the retarding method is applied, the secondary electrons passing through the objective lens should be deflected to the outside of the optical axis and then are injected into the spectrometer. Further, the secondary electrons passing through the objective lens are spatially scattered, thus requiring a convergence mechanism in order to increase the number of secondary electrons to be injected into the spectrometer.

On the other hand, in the retarding optical system, changing the energy injected into the sample of the primary electron to change the observation target is achieved by changing the retarding voltage $V_r$. Here, the energy of the secondary electron changes when $V_r$ is changed, and there is a problem that the focus position of the secondary electron changes. Further, the relationship between the energy resolution $\Delta E$ of the spectrometer, and the energy $E_p$ of the secondary electron, which is detected passing through the spectrometer, is expressed by the following equation.

Equation 1

$$\frac{\Delta E}{E_p} = R \tag{1}$$

Here, R is a unique constant determined by the size and shape of the spectrometer as well as the dimensions of the slit. When the retarding method is used, the secondary electron is accelerated by the voltage $V_r$ applied to the sample. In other words, there is a problem that when $V_r$ is changed for a change in the observation target or the like, the energy of the secondary electron injected into the spectrometer also changes, resulting in a change in the energy resolution $\Delta E$.

An object of the present invention is to provide an SEM using a retarding method and having an electron spectroscopy system, in which the number of electrons injected into a spectrometer and the energy resolution do not change even if the retarding voltage $V_r$ is changed, and to provide a control method of the SEM.

Solution to Problem

In order to achieve the above object, the present invention provides an SEM including: an electron source; a first deflector that deflects a primary electron beam emitted from the electron source; a converging lens that focuses the primary electron beam deflected by the first deflector; a second deflector that deflects a secondary electron from a sample, which is generated by the first electron beam focused by the converging lens, to the outside of the optical axis of the primary electron beam; a voltage applying unit that applies a negative voltage to the sample to decelerate the primary electron beam; a spectrometer for dispersing the secondary electron; a detector that detects the secondary electron passing through the spectrometer; an electrostatic lens provided between the second deflector and the spectrometer; and a voltage control unit that controls the voltage applied to the electrostatic lens based on the negative voltage applied to the sample. The electrostatic lens allows the deflecting action to be overlapped with the converging action.

Further, in order to achieve the above object, the present invention provides a control method of an SEM including: a deflector that deflects a secondary electron from a sample, which is generated by focusing a primary electron beam emitted from an electron source and by irradiating the sample with the primary electron beam, to the outside of the optical axis of the primary electron beam; a spectrometer for dispersing the secondary electron; a detector that detects the secondary electron passing through the deflector; and an electrostatic lens provided between the deflector and the spectrometer, allowing the deflecting action to be overlapped with the converging action. The control method applies a negative voltage to the sample to decelerate the primary electron beam, to control a first bias voltage applied to the electrostatic lens based on the negative voltage applied to the sample.

Advantageous Effects of Invention

According to the present invention, it is possible to perform the energy dispersion of the secondary electron, without changing the number of electrons injected into the electrometer and the energy resolution even if the retarding voltage $V_r$ is changed, by using the retarding method.

DESCRIPTION OF EMBODIMENTS

Figure 1:
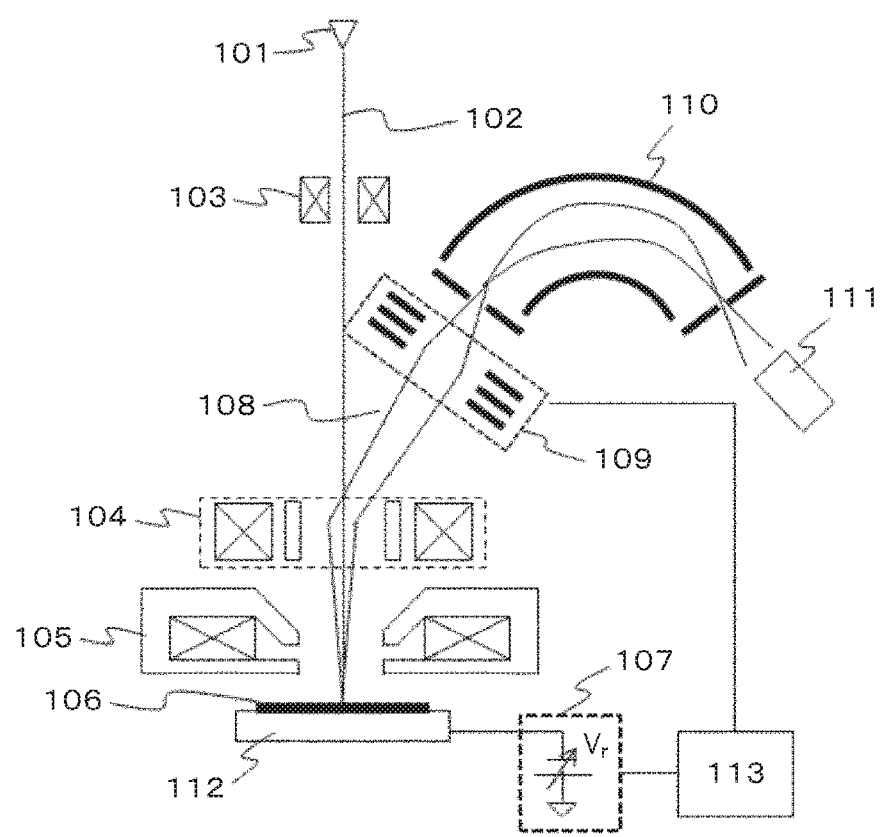
FIG. 1 is a schematic block diagram of an overall SEM according to a first embodiment.

Hereinafter, various embodiments for implementing the present invention will be described in detail with reference to the accompanying drawings. In each of the embodiments, like reference numerals refer to like parts throughout the drawings.

First Embodiment

The first describes an example of an SEM, as a first embodiment, including: an electron source; a first deflector that deflects a first electron beam emitted from the electron source; a converging lens that focuses the primary electron beam deflected by the first deflector; a second deflector that deflects a secondary electron from a sample, which is generated by the focused primary electron beam; a voltage applying unit that applies a negative voltage to the sample to decelerate the primary electron beam; a spectrometer for dispersing the secondary electron; a detector that detects the secondary electron passing through the spectrometer; an electrostatic lens provided between the second deflector and the spectrometer; and a voltage control unit that controls the voltage applied to the electrostatic lens based on the negative voltage applied to the sample. The electrostatic lens allows the deflecting action to be overlapped with the converging action.

FIG. 1 is a diagram showing the configuration of the SEM according to the first embodiment. In the SEM shown in FIG. 1, a primary electron 102 generated by an electron source 101 is deflected and scanned by a deflector 103. After passing through a secondary electron deflector 104, the primary electron is narrowed down by an objective lens 105 that functions as a converging lens. Then, the primary electron is injected into a sample 106. Note that the objective lens 105 is an example of the converging lens, and other converging lens can be provided on the optical axis as needed.

The sample 106 is placed on a sample holder 112. The sample 106 and the sample holder 112 are electrically connected to each other. A retarding voltage can be applied to the sample holder 112 by a retarding power supply 107 that functions as a voltage applying unit. The primary electron 102 is decelerated by the retarding voltage and is injected into the sample 106. Hereinafter, the voltage applied by the retarding power supply 107, which is the voltage applying unit, will be referred to as the retarding voltage $V_r$ (<0).

A secondary electron 108 is generated due to irradiation of the sample 106 with the primary electron 102. The secondary electron 108 is accelerated by the retarding voltage $V_r$. Then, the secondary electron 108 is deflected to the outside of the optical axis of the primary electron 102 by the secondary electron deflector 104. Here, the secondary electron deflector 104 is the optical element in which the electric field and the magnetic field are orthogonal to each other. The magnitude of the electric field and the magnitude of the magnetic field are set to conditions (hereinafter, Vienna conditions) under which the primary electron 102 is not deflected in the secondary electron deflector 104. In Vienna conditions, the secondary electron 108, which is injected into the secondary electron deflector 104 from the opposing direction to the primary electron 102, is deflected to the outside of the optical axis in the secondary electron deflector 104.

The secondary electron 108 deflected to the outside of the optical axis is subjected to the converging and deflecting actions. After that, the secondary electron 108 is injected into a spectrometer 110. The spectrometer 110 has a feature that allows only the secondary electron 108 with a specific energy $E_p$ to pass through. The secondary electron 108 dispersed after passing through the spectrometer 110 is detected by a detector 111.

In the description of the present embodiment, the SEM is provided with a sector-type electrostatic deflection spectrometer using two cylindrical electrodes as the configuration of the spectrometer 110. However, the effect of the present embodiment can also be obtained by using spectrometers of other shapes, for example, semispherical electrometers of semispherical shape and the like. It is possible to select $E_p$ by changing a voltage $\pm V_d$ that is applied to the two cylindrical electrodes of the spectrometer 110. Further, it is possible to obtain the energy spectrum of the secondary electron 108 by sweeping $V_d$.

Here, since the secondary electron 108 is accelerated by the retarding voltage $V_r$, the magnitude of the deflecting and converging action in the electrostatic lens 109 changes when $V_r$ is changed. Thus, the present embodiment shows the configuration of the electrostatic lens 109 in which the number of electrons injected into the spectrometer 110 with respect to the secondary electron 108 does not change even if the retarding voltage $V_r$ is changed, as well as the voltage control method.

Even in the case where the secondary electron 108 is designed to be perpendicularly injected into the spectrometer 110, the secondary electron 108 is deflected due to assembling accuracy and disturbances, such as leakage field of the objective lens, and is injected into the spectrometer 110. The incident angle of the secondary electron 108, which affects the energy resolution, is desirably as near perpendicular to the spectrometer 110 as possible. Further, also in the case where the secondary electron 108 is spatially scattered and injected into the spectrometer 110, the energy resolution is reduced. Thus, an optical element is required to allow the secondary element 108 to be focused, deflected, and injected into the spectrometer 110. However, when the size of the optical element for focusing and deflecting the secondary element 108 is increased, the length of the entire system is increased, and noise such as vibration occurs. For this reason, it is desirable that the optical element be compact. In the present embodiment, the electrostatic lens 109 is used in the SEM.

Figure 2:
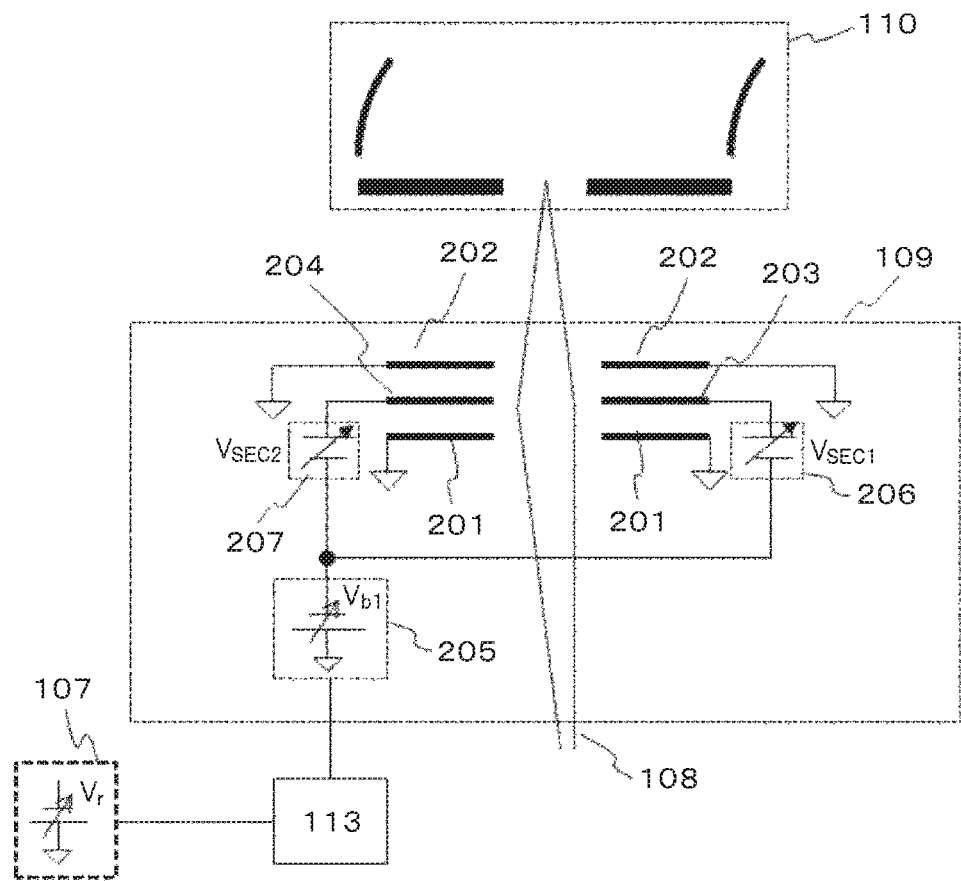
FIG. 2 is an enlarged view of an electrostatic lens according to the first embodiment.

FIG. 2 is an enlarged view of the electrostatic lens 109 of the present embodiment. The electrostatic lens 109 includes two electrostatic lens electrodes A201 and B202 that are grounded, as well as divided electrode static electrodes C203 and C'204 in order to apply different voltages. A voltage obtained by superimposing a negative first bias voltage $V_{b1}$ (<0), which is applied by a bias power supply A205, with a voltage $V_{SEC1}$ of an electrostatic lens power supply A206 is applied to the electrostatic lens electrode C203. Further, a voltage obtained by superimposing the negative first bias voltage $V_{b1}$ (<0) with a voltage $V_{SEC2}$ of an electrostatic lens power supply A207 is applied to the electrostatic lens electrode C'204.

Figure 3:
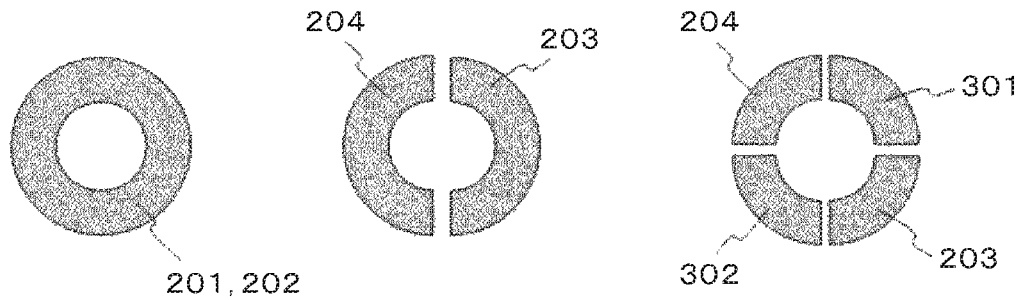
FIG. 3 is a view showing the shapes of the electrostatic lens electrodes according to the first embodiment.

Here, as shown on the left side of FIG. 3, the electrostatic lens electrode A201 and the electrostatic lens electrode B202 have an annular shape, or a doughnut shape. It is assumed that, as shown in the center of FIG. 3, the electrostatic lens electrode C203 and the electrostatic lens electrode C'204 are formed by diving the shape of the electrostatic lens electrode A201 and the shape of the electrostatic lens electrode B201. Further, as in the case of four division electrodes shown in the right side of FIG. 3, two or more division electrodes can also be used. The unidirectional deflecting action can be obtained in the case of two division electrodes, while the bidirectional deflecting action can be obtained in the case of four or more division electrodes. In the case of the four division electrodes, as shown in the right side of FIG. 3, an electronic lens electrode C"301 and an electrostatic lens electrode C'"302 are also provided, in addition to the electrostatic lens electrode C203 and the electrostatic lens electrode C'204.

Hereinafter, the function of the electrostatic lens 109 will be described in the case of two division electrodes, the electrostatic lens electrode C 203 and the electrostatic lens electrode C' 204. Here, when $V_{SEC1} \ne V_{SEC2}$ in the electrostatic lens 109 of the present embodiment, it is possible to obtain both the deflecting action and the converging action. Further, since the deflecting action is overlapped with the converging action in the electrostatic lens electrode C203 and the electrostatic lens electrode C'204, it is possible to achieve a compact configuration as a whole. Practically, it is possible to configure the electrostatic lens 109 with an entire thickness of approximately 6 mm. Note that when $V_{SEC1} = V_{SEC2}$, the electrostatic lens 109 can obtain only the converging action.

Since the energy of the secondary electron 108 changes when the retarding voltage $V_r$ is changed, the focus position of the secondary electron 108 in the electrostatic lens 109 is also changed. In order to keep the focus position of the secondary electron 108 constant at any value of the retarding voltage $V_r$, the first bias voltage $V_{b1}$ applied by the bias power supply A205 is controlled according to the retarding voltage $V_r$. Thus, the bias power supply A205 and the retarding power supply 107 are connected to a voltage control device 113 that functions as the voltage control unit. In this way, the first bias voltage $V_{b1}$ is also changed in conjunction with changes in the retarding voltage $V_r$.

Note that the device manufacturer determines in advance the relationship between $V_{b1}$ and $V_r$ and implements the control algorithm that is changed in conjunction with the voltage control device 113. Thus, the user only sets the retarding voltage $V_r$. Here, the voltage control device 113, which is the voltage control unit, can be configured with a computer including a central processing unit (CPU) for performing the control algorithm to be implemented, a memory for storing programs and data, and the like. The relationship between $V_r$ and $V_{b1}$, $V_{SEC1}$, as well as $V_{SEC2}$ varies depending on the assembling accuracy of each device, and the like, so that it is necessary to set the retarding voltage $V_r$ for each device.

Figure 8:
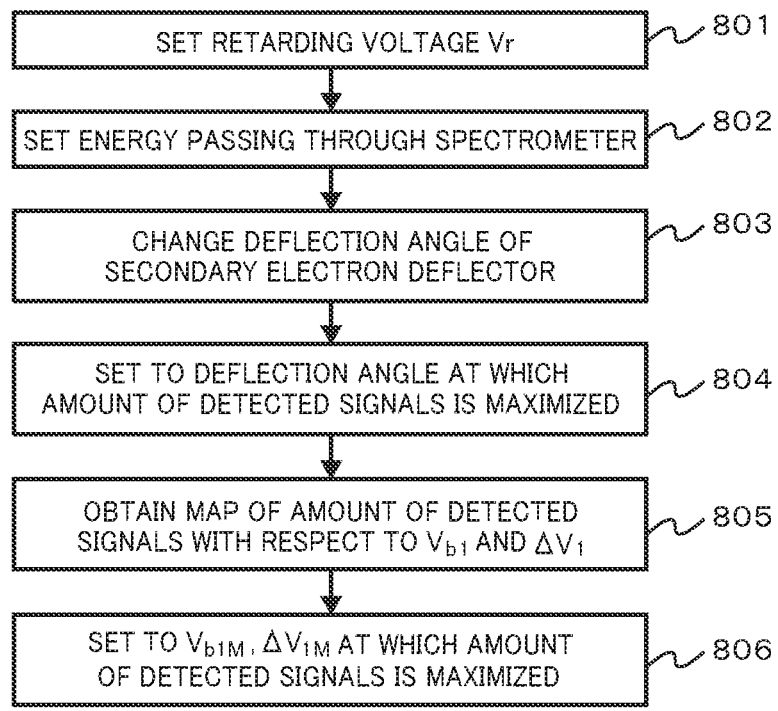
FIG. 8 is a flow chart showing a method of adjusting the electrostatic lens voltage and the retarding voltage according to each of the embodiments.
Figure 9:
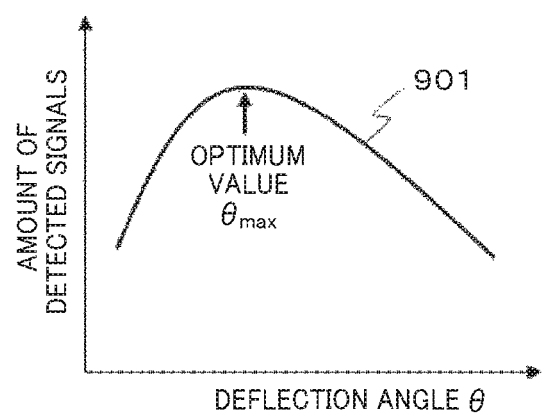
FIG. 9 is a view showing a method of determining the secondary electron deflection angle according to each of the embodiments.

Here, the method of adjusting the relationship between $V_r$ and $V_{b1}$, $V_{SEC1}$ $V_{SEC2}$ as well as $V_r$ will be described with reference to the process flow of FIG. 8. First, the user sets the retarding voltage $V_r$ (<0) (801) and applies to the sample holder 112. Next, the user sets the $E_p$ passing through the spectrometer 110 to be equal to the negative voltage applied to the sample, that is, the energy $E_p$ passing through the spectrometer 110 is equal to $-eV_r$ (802). Here, e is the elementary charge. Next, the user monitors the amount of detected signals of the detector 111 while continuously changing the deflection angle θ of the secondary electron 108 by the secondary electron deflector 104 (803). Then, the user sets the deflection angle $θ_{max}$ at which the amount of detected signals is maximized (804). FIG. 9 is a graph 901 showing the relationship between the deflection angle θ and the amount of detected signals. In the graph 901, the deflection angle $θ_{max}$ is the optimum value.

Figure 10:
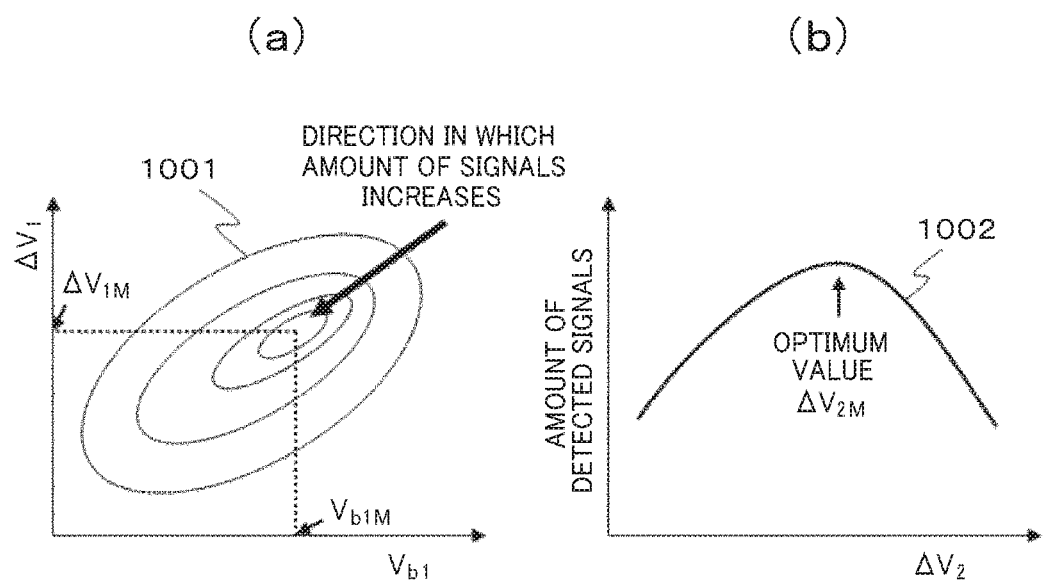
FIG. 10 is a view showing a method of determining the optimum value of the electrostatic lens voltage according to each of the embodiments.

Next, the method obtains the contour drawing (map) of the amount of detected signals with respect to $V_{b1}$ and $\Delta V_1$ (=$V_{SEC1} - V_{SEC2}$) in the optimum value $θ_{max}$ (805). In a contour drawing 1001 shown in (a) of FIG. 10, $V_{b1M}$ and $\Delta V_{1M}$ are the optimum values with the highest amount of detected signals.

In the case of four division electrodes like the electrostatic lens electrode C 203, the electrostatic lens electrode C' 204 the electrostatic lens electrode C" 301, and the electrostatic lens electrode C'" 302 as shown in the right side of FIG. 3, $\theta_{max}$, $V_{b1M}$, and $\Delta V_{1M}$ are first determined by the method described above. Then, voltages $V_{SEC3}$ and $V_{SEC4}$ are applied to the electrostatic lens electrode C" 301 and the electrostatic lens electrode C'" 302, respectively. Then, the optimum value can be determined by monitoring the amount of detected signals with respect to $\Delta V_2$ ($=V_{SEC3}-V_{SEC4}$), and by obtaining the voltage $\Delta V_{2M}$ at which the amount of detected signals is maximized.

Figure 4:
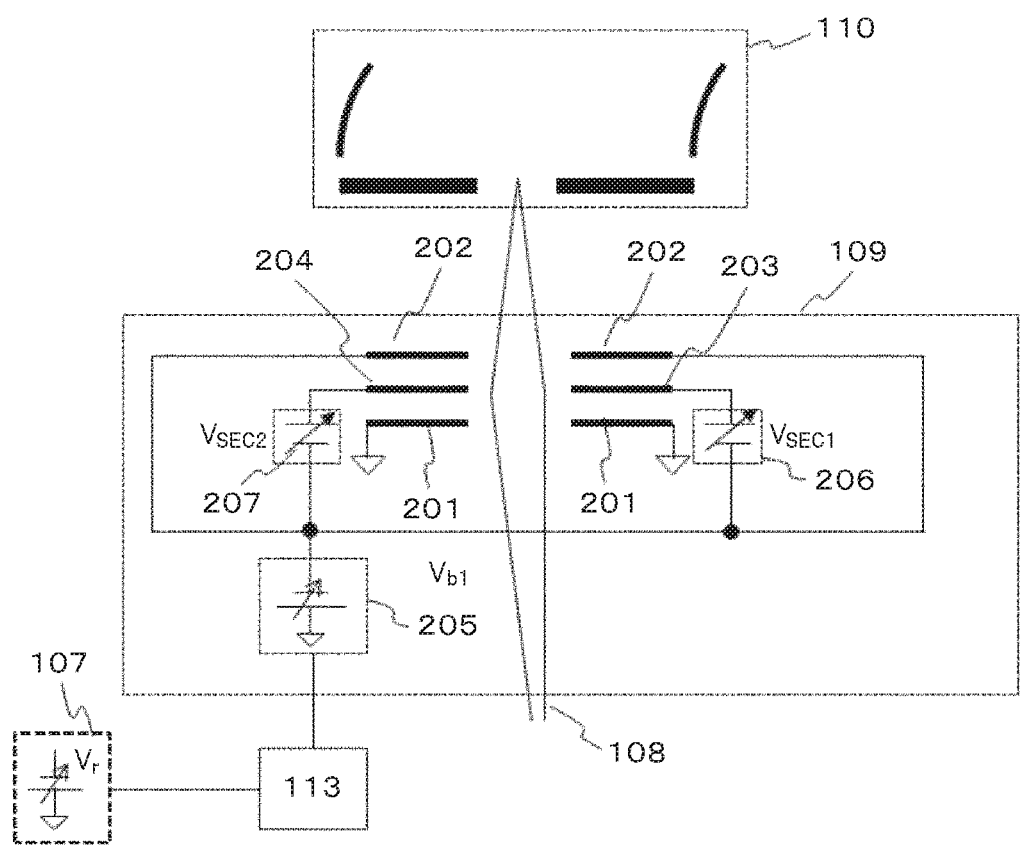
FIG. 4 is a view showing a method of applying a voltage to the electrostatic lens electrodes according to the first embodiment.

Note that in the electrostatic lens 109 of the present embodiment, the electrode A201 and the electrostatic lens electrode B202 shown in FIG. 2 are not required to be constantly grounded. For example, as shown in FIG. 4, the first bias voltage $V_{b1}$ can be applied to the electrostatic lens electrode B202. In this case, it is necessary to perform the adjustment method shown in the flow of FIG. 8 separately.

With the configuration of the first embodiment described above, it is possible to provide the SEM that can perform the energy dispersion of the secondary electron, without changing the number of electrons injected into the spectrometer even if the retarding voltage $V_r$ is changed.

Second Embodiment

The second embodiment is an example of an SEM in which a negative second bias voltage is applied to the entire spectrometer which is then floated, and in which the bias voltage is controlled according to the negative retarding voltage applied to the sample. In the SEM, the voltage for discriminating the secondary electron by energy is superimposed with the negative second bias voltage. Further, the SEM also includes an input unit for the user to input the energy resolution of the spectrometer, so that the difference between the negative second bias voltage applied to the spectrometer and the negative voltage applied to the sample is controlled according to the value of the energy resolution that is input from the input unit.

Figure 5:
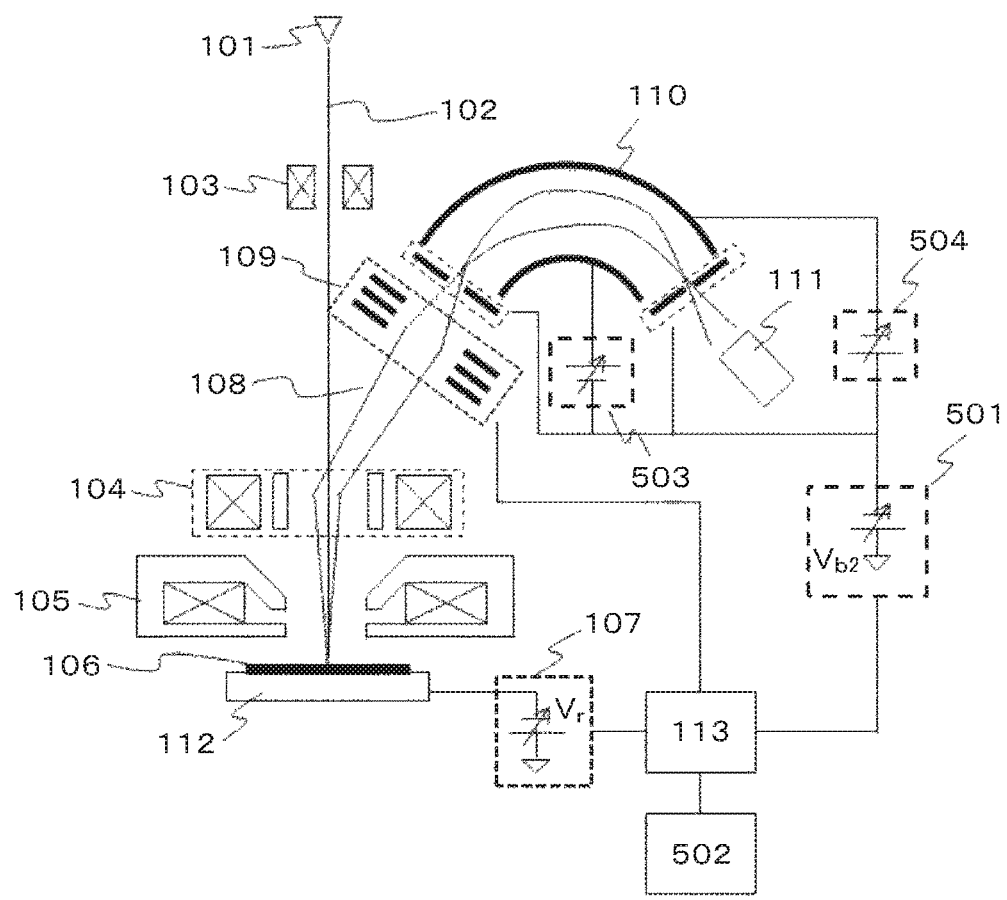
FIG. 5 is a schematic block diagram of an overall SEM according to a second embodiment.

FIG. 5 shows the configuration of the SEM according to the second embodiment. As shown in the figure, the SEM according to the present embodiment is configured by adding a bias power supply B501, a $\Delta E$ input unit 502, a spectrometer power supply A503, and a spectrometer power supply B504 to the configuration of the first embodiment. The whole spectrometer 110 is floated with the second bias voltage $V_{b2}$ ($<0$) by the bias power supply B501. Then, a voltages $\pm V_d$ is superimposed with $V_{b2}$ and the superimposed voltages is applied to the cylindrical electrode by the spectrometer power supply A503 and by the spectrometer power supply B504 so that the orbits of the secondary electron 108 are separated according to their energies.

In the retarding optical system employed in the present embodiment, the energy of the secondary electron 108 changes when the retarding voltage $V_r$ is changed. On the other hand, the relationship between the energy resolution $\Delta E$ of the spectrometer 110 and the energy $E_p$ of the secondary electron 108, which is detected passing through the spectrometer 110, is expressed by the (1) equation described above. Here, given that the magnitude of $V_r$ is several kV, and given the "true" secondary electron of 50 eV or less as the secondary electron 108, the following relation is derived under the condition of $V_{b2}$=0 V.

Equation 2

$$E_p \approx -eV_r \quad (2)$$

This yields the following equation.

Equation 3

$$\Delta E \approx -eV_r \cdot R \quad (3)$$

The energy resolution $\Delta E$ varies according to $V_r$. For example, in the case of R=1%, $\Delta E$=10 eV at $V_r$=−1000 V but $\Delta E$=50 eV at $V_r$=−5000 V. Such a variation of $\Delta E$ should be an obstacle to obtaining the quantitative information by dispersing the "true" secondary electron of 50 eV or less.

Thus, in the present embodiment, the whole spectrometer 110 is floated with the second bias voltage $V_{b2}$ by the bias source B501. Here, the second bias voltage $V_{b2}$ and the retarding voltage Vr are determined so as to satisfy the following relationship.

Equation 4

$$V_r < V_{b2} < 0 \quad (4)$$

When the spectrometer 110 is floated with the second bias voltage $V_{b2}$, the secondary electron 108 is decelerated by the bias voltage $V_{b2}$ and is injected into the spectrometer 110. Thus, $E_p$ and $\Delta E$ can be expressed by the following equations.

Equation 5

$$E_p \approx -e(V_r - V_{b2}) \quad (5)$$

Equation 6

$$\Delta E \approx -e(V_r - V_{b2}) \cdot R \quad (6)$$

Thus, by changing the second bias voltage $V_{b2}$ in conjunction with changes in the retarding voltage $V_r$, it is possible to keep the energy resolution $\Delta E$ constant. In addition, by reducing the difference between the voltage $V_r$ and the voltage $V_{b2}$, it is possible to increase the energy resolution $\Delta E$ without changing the configuration of the spectrometer 110. The control of the voltages $V_r$ and $V_{b2}$ is performed by the voltage control device 113 to which the retarding power supply 107 and the bias power supply B501 are connected. For example, the voltage control device 113 controls to satisfy the following equation.

Equation 7

$$|V_r - V_{b2}| = \text{const.} \quad (7)$$

Figure 6:
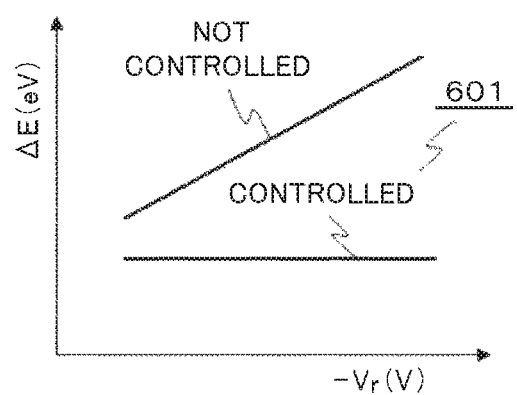
FIG. 6 is a view showing the relationship between the energy resolution and the retarding bias voltage according to the second embodiment.

In this case, as shown in a graph 601 of FIG. 6, the energy resolution $\Delta E$ is kept constant when the control of the (7) equation is performed, even if the retarding voltage $V_r$ is changed. However, when the control is not performed, the energy resolution $\Delta E$ changes in conjunction with changes in $V_r$. Changes in $V_r$ correspond to changes in the energy of the primary electron 102 that is injected into the sample 106. Thus, by performing the control of the (7) equation, it is possible to quantitatively compare the energy spectra of the secondary electron 108 obtained at different energies of the primary electron 102 injected into the sample 106.

In the configuration of the present embodiment, it is also possible that the user freely sets the energy resolution $\Delta E$. The user inputs a desired $\Delta E$ and retarding voltage $V_r$ to the $\Delta E$ input unit 502 connected to the voltage control device 113. Then, by the control of the voltage control device 113, the second bias voltage $V_{b2}$ determined by the following equation is output from the bias power supply B501.

Equation 8

$$V_{b2} = V_r + \frac{1}{R}\frac{\Delta E}{e} \quad (8)$$

Note that the constant R is determined by the configuration of the spectrometer 110, for example, by the size of the electrode, so that the constant R is stored in the voltage control device 113 in advance on the device manufacture side.

According to the present embodiment, it is possible to provide an SEM that can perform the energy dispersion of the secondary electron, without changing the number of electrons injected into the spectrometer as well as the energy resolution, even if the retarding voltage $V_r$ is changed. In addition, since the user can freely set the energy resolution, it is possible to provide an easy-to-use SEM.

Third Embodiment

Figure 7:
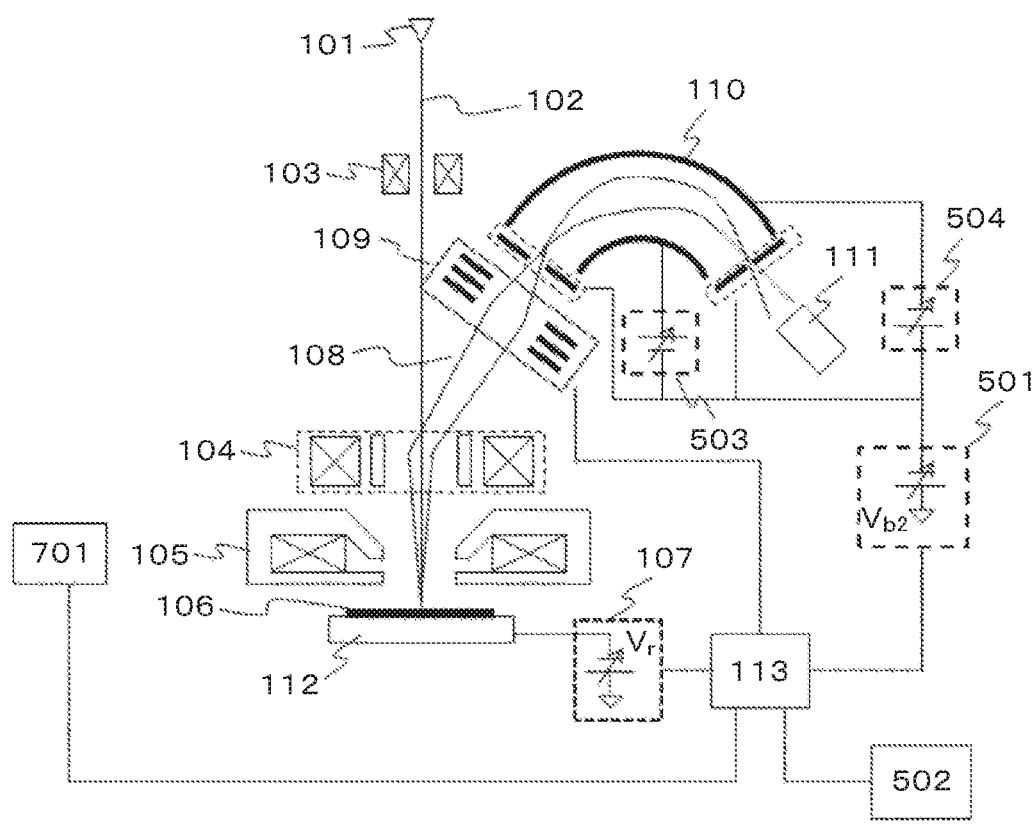
FIG. 7 is a schematic block diagram of an overall SEM according to a third embodiment.

The third embodiment is an example of an SEM which also includes a potential meter that measures the surface potential of the sample, measuring the potential of the sample by the potential meter before irradiation of the primary electron on the sample, to change the negative bias voltage in conjunction with changes in the potential of the sample. FIG. 7 is a diagram of the configuration of the SEM according to the present embodiment, in which a potential meter 701 is added to the configuration of the second embodiment shown in FIG. 5.

When an insulator is observed by the SEM, the retarding voltage $V_r$ that is applied to the sample holder 112 by the retarding power supply 107 may differ from the potential $V_s$ of the sample surface. If the voltage $V_r$ is different from the potential $V_s$, the bias voltages $V_{b1}$ and $V_{b2}$ may deviate from the optimal points because the bias voltages $V_{b1}$ and $V_{b2}$ are controlled with respect to the retarding voltage $V_r$ in the configurations of the first and second embodiments.

In the present embodiment, the above problem is solved by controlling the bias voltages $V_{b1}$ and $V_{b2}$ with respect to the potential $V_s$ of the sample surface. More specifically, the surface potential $V_s$ is measured by the potential meter 701 before the sample 106 is observed by the SEM. As the potential meter 701, a measurement device such as Kelvin probe is used. However, it is enough that the potential meter 701 measures the potential $V_s$ of the surface of the sample 106, and the present invention is not limited to the Kelvin probe.

As shown in FIG. 7, the potential meter 701 is connected to the voltage control device 113. In the control of the bias voltages $V_{b1}$ and $V_{b2}$ described in the first and second embodiments, the voltages are controlled with respect to the retarding voltage $V_r$. However, in the present embodiment, the control is performed based on the surface potential $V_s$ measured by the potential meter 701. More specifically, for example, $V_r$ in the (8) equation is replaced by $V_s$.

When the potential measurement is performed by the potential meter 701, the voltage control device 113 is programmed to control the bias voltages $V_{b1}$ and $V_{b2}$ with respect to the surface potential $V_s$. Thus, it is possible to obtain the optimum bias voltages $V_{b1}$ and $V_{b2}$, without the need for the user to perform any adjustment operation.

According to the present embodiment, it is possible to optimally control the bias voltages, even if the voltage $V_r$ applied to the sample holder 112 by the retarding power supply is different from the potential $V_s$ of the sample surface.

Note that the present invention is not limited to the embodiments described above, and includes various modifications. For example, the above embodiments have been described in detail for a better understanding of the present invention, and the present invention is not necessarily limited to those with all of the configurations described. Further, a part of the configuration of an embodiment can be replaced with the configuration of another embodiment, and the configuration of an embodiment can be added to the configuration of another embodiment. Furthermore, addition, deletion, and replacement of another configuration can be performed on a part of the configuration of each embodiment.

Further, the above description assumes that different programs are created to implement some or all of the configurations, the functions, the voltage control device, and the like. However, it goes without saying that some or all of them can be implemented in hardware, for example, by designing the integrated circuit, or using other methods.

LIST OF REFERENCE SIGNS

101: electron source
102: primary electron
103: deflector
104: secondary electron deflector
105: objective lens
106: sample
107: retarding power supply
108: secondary electron
109: electrostatic lens
110: spectrometer
111: detector
112: sample holder
113: voltage control device
201: electrostatic lens electrode A
202: electrostatic lens electrode B
203: electrostatic lens electrode C
204: electrostatic lens electrode C'
205: bias power supply A
206: electrostatic lens power supply A
207: electrostatic lens power supply B
301: electrostatic lens electrode C''
302: electrostatic lens electrode C'''
501: bias power supply B
502: ΔE input unit
503: spectrometer power supply A
504: spectrometer power supply B
601: graph
701: potential meter
901: graph
1001: contour map
1002: graph

The invention claimed is:

1. A scanning electron microscope comprising:
an electron source;
a first deflector that deflects a primary electron beam emitted from the electron source;
a converging lens that focuses the primary electron beam deflected by the first deflector;
a second deflector that deflects a secondary electron from a sample, which is generated by the primary electron beam that is focused by the converging lens, to outside of an optical axis of the primary electron beam;
a retarding power supply that applies a negative voltage to the sample to decelerate the primary electron beam;
a spectrometer that disperses the secondary electron;
a detector that detects the secondary electron passing through the spectrometer;
an electrostatic lens provided between the second deflector and the spectrometer; and
a voltage controller configured to control voltages applied to the electrostatic lens based on the negative voltage applied to the sample,
wherein the electrostatic lens includes at least two grounded electrodes and at least two divided electrodes,
wherein the divided electrodes are located between the two grounded electrodes,
wherein the voltage controller is configured to superimpose a negative first bias voltage, which is controlled based on the negative voltage applied to the sample, with a first voltage, and to superimpose the negative first bias voltage with a second voltage, and
wherein the voltage controller is configured to apply the superimposed first voltage and the second superimposed second voltage, which are different voltages, to the divided electrodes to provide a deflecting action that is overlapped with a converging action with the electrostatic lens.

2. A scanning electron microscope comprising:
an electron source;
a first deflector that deflects a primary electron beam emitted from the electron source;
a converging lens that focuses the primary electron beam deflected by the first deflector;
a second deflector that deflects a secondary electron from a sample, which is generated by the primary electron beam that is focused by the converging lens, to outside of an optical axis of the primary electron beam;
a retarding power supply that applies a negative voltage to the sample to decelerate the primary electron beam;
a spectrometer that disperses the secondary electron;
a detector that detects the secondary electron passing through the spectrometer;
an electrostatic lens provided between the second deflector and the spectrometer; and
a voltage controller configured to control voltages applied to the electrostatic lens based on the negative voltage applied to the sample,
wherein the electrostatic lens includes a grounded electrode, at least two divided electrodes, and an undivided electrode,
wherein the divided electrodes are located between the grounded electrode and the undivided electrode,
wherein the voltage controller is configured to superimpose a negative first bias voltage, which is controlled based on the negative voltage applied to the sample, with a first voltage, and to superimpose the negative first bias voltage with a second voltage, and
wherein the voltage controller is configured to apply the superimposed first and second voltages to the divided electrodes while applying the first bias voltage to the undivided electrode.

3. The scanning electron microscope according to claim 2, wherein the divided electrodes are separated and define an annular shape.

4. The scanning electron microscope according to claim 2, wherein the voltage controller is further configured to set the first bias voltage to maximize an amount of detected signals of the detector when an energy passing through the spectrometer is the same as the negative voltage applied to the sample.

5. The scanning electron microscope according to claim 2, wherein the spectrometer is an electrostatic deflection type spectrometer, and
wherein the voltage controller is further configured to superimpose one or more discriminating voltages for discriminating the secondary electron by energy with a second bias voltage, and to apply the one or more superimposed discriminating voltages to the spectrometer.

6. The scanning electron microscope according to claim 5, wherein the voltage controller is further configured to control an absolute value of the second bias voltage to be smaller than an absolute value of the negative voltage applied to the sample.

7. The scanning electron microscope according to claim 5, wherein the voltage controller is further configured to control a difference between the second bias voltage and the negative voltage applied to the sample to be constant.

8. The scanning electron microscope according to claim 5, further comprising:
a potential meter that measures a surface potential of the sample,
wherein the potential of the sample is measured by the potential meter before irradiation of the sample with the primary electron beam, and
wherein the voltage controller is further configured to change the second bias voltage in conjunction with changes in the measured potential of the sample.

9. The scanning electron microscope according to claim 1, wherein the divided electrodes are separated and define an annular shape.

10. The scanning electron microscope according to claim 1,
wherein the voltage controller is further configured to set the first bias voltage to maximize an amount of detected signals of the detector when an energy passing through the spectrometer is the same as the negative voltage applied to the sample.

11. The scanning electron microscope according to claim 1,
wherein the spectrometer is an electrostatic deflection type spectrometer, and
wherein the voltage controller is further configured to superimpose one or more discriminating voltages for discriminating the second electron by energy with a second bias voltage, and to apply the one or more superimposed discriminating voltages to the spectrometer.

12. The scanning electron microscope according to claim 11,
wherein the voltage controller is further configured to control an absolute value of the second bias voltage to be smaller than an absolute value of the negative voltage applied to the sample.

13. The scanning electron microscope according to claim 11,
wherein the voltage controller is further configured to control a difference between the second bias voltage and the negative voltage applied to the sample to be constant.

14. The scanning electron microscope according to claim 13, further comprising:
an input unit for inputting an energy resolution of the spectrometer,
wherein the voltage controller is further configured to control the difference between the second bias voltage and the negative voltage which is applied to the sample according to a value of the energy resolution input with the input unit.

15. The scanning electron microscope according to claim 11, further comprising:
a potential meter that measures a surface potential of the sample,
wherein the potential of the sample is measured by the potential meter before irradiation of the sample with the primary electron beam, and
wherein the voltage controller is further configured to change the second bias voltage in conjunction with changes in the measured potential of the sample.

16. The scanning electron microscope according to claim 15,
wherein the voltage controller is further configured to control a difference between the second bias voltage and the measured potential of the sample to be constant.

17. A scanning electron microscope control method of a comprising:
providing a scanning electron microscope which includes:
a deflector that deflects a secondary electron from a sample, which is generated by focusing a primary electron beam emitted from an electron source and by irradiating the sample with the primary electron beam, to outside of the optical axis of the primary electron beam,
a spectrometer that disperses the secondary electron,
a detector that detects the secondary electron passing through the deflector, and
an electrostatic lens that is provided between the deflector and the spectrometer, the electrostatic lens including at least two grounded electrodes and at least two divided electrodes, and the divided electrodes are located between the two grounded electrodes;
applying a negative voltage to the sample to decelerate the primary electron beam;
superimposing a negative first bias voltage, which is controlled based on the negative voltage applied to the sample, with a first voltage;
superimposing the negative first bias voltage with a second voltage; and
applying the superimposed first voltage and the second superimposed second voltage, which are different voltages, to the divided electrodes to provide a deflecting action that is overlapped with a converging action with the electrostatic lens.

18. The scanning electron microscope control method according to claim 17, further comprising:
setting the first bias voltage to maximize an amount of detected signals of the detector when an energy passing through the spectrometer is the same as the negative voltage applied to the sample.

19. The scanning electron microscope control method according to claim 17, further comprising:
superimposing a negative second bias voltage with at least one discriminating voltage for discriminating the second electron by energy;
applying the superimposed at least one discriminating voltage to the spectrometer; and
controlling a difference between the second bias voltage and the negative voltage applied to the sample is controlled to be constant.

20. The scanning electron microscope control method of the scanning electron microscope according to claim 17, further comprising:
superimposing a negative second bias voltage with at least one discriminating voltage for discriminating the secondary electron by energy;
applying the superimposed at least one discriminating voltage to the spectrometer; and
controlling a difference between the second bias voltage and the negative voltage applied to the sample according to an energy resolution value.

* * * * *